US012305174B2

(12) United States Patent
Marizcurrena et al.

(10) Patent No.: US 12,305,174 B2
(45) Date of Patent: May 20, 2025

(54) GENETICALLY MODIFIED BACTERIA PRODUCING THREE DNA REPAIR ENZYMES AND METHOD FOR THE EVALUATION OF DNA REPAIR ACTIVITY

(71) Applicants: Universidad de la República, Montevideo (UY); MINISTERIO DE DEFENSA NACIONAL—INSTITUTO ANTÁRTICO URUGUAYO, Montevideo (UY)

(72) Inventors: Juan José Marizcurrena, Montevideo (UY); Susana Castro Sowinski, Montevideo (UY)

(73) Assignees: UNIVERSIDAD DE LA REPUBLICA, Montevideo (UY); MINISTERIO DE DEFENSA NACIONAL—INSTITUTO ANTARTICO URUGUAYO, Montevideo (UY)

( * ) Notice: Subject to any disclaimer, the term of this patent is extended or adjusted under 35 U.S.C. 154(b) by 907 days.

(21) Appl. No.: 17/273,627

(22) PCT Filed: Sep. 4, 2019

(86) PCT No.: PCT/BR2019/050373
§ 371 (c)(1),
(2) Date: Mar. 4, 2021

(87) PCT Pub. No.: WO2020/047637
PCT Pub. Date: Mar. 12, 2020

(65) Prior Publication Data
US 2022/0042024 A1 Feb. 10, 2022

Related U.S. Application Data

(60) Provisional application No. 62/726,780, filed on Sep. 4, 2018.

(51) Int. Cl.
C12N 15/70 (2006.01)
C12N 1/20 (2006.01)
C12N 9/88 (2006.01)
C12Q 1/527 (2006.01)
C12Q 1/683 (2018.01)
C12R 1/19 (2006.01)

(52) U.S. Cl.
CPC .......... C12N 15/70 (2013.01); C12N 1/205 (2021.05); C12N 9/88 (2013.01); C12Q 1/527 (2013.01); C12Q 1/683 (2013.01); C12R 2001/19 (2021.05); C12Y 401/99003 (2013.01); G01N 2333/245 (2013.01); G01N 2333/988 (2013.01)

(58) Field of Classification Search
CPC .......... C12N 15/70; C12N 1/205; C12N 9/88; C12Y 401/99003
See application file for complete search history.

(56) References Cited

U.S. PATENT DOCUMENTS

| 10,459,339 | B2 | 10/2019 | Fukuoka et al. |
| 2004/0057917 | A1* | 3/2004 | Wolf ............ A61K 36/886 424/59 |
| 2006/0002884 | A1* | 1/2006 | Golz-Berner .......... A61Q 19/08 424/769 |
| 2006/0257509 | A1 | 11/2006 | Zimmerman et al. |
| 2009/0117060 | A1 | 5/2009 | Golz-Berner et al. |

FOREIGN PATENT DOCUMENTS

| CN | 1624120 A | 6/2005 |
| CN | 101144088 A | 3/2008 |
| CN | 103212066 A | 7/2013 |
| CN | 103966193 A | 8/2014 |
| CN | 105062999 A | 11/2015 |
| CN | 105087535 A | 11/2015 |
| EP | 1634576 A1 | 3/2006 |
| EP | 2223679 A2 | 9/2010 |
| KR | 018068 B1 | 3/1999 |
| PT | 2717907 E | 8/2015 |
| WO | WO-2014011611 A1 | 1/2014 |
| WO | WO-2014166137 A1 | 10/2014 |

OTHER PUBLICATIONS

Heijde et al. Plant, Cell and Environment, 2010, 33, 1614-1626 (Year: 2010).*
Marizcurrena et al. Extremophiles, 2017, 21, 409-418 (Year: 2017).*
Genbank, KX118295, p. 1 [retrieved on Mar. 29, 2024]. Retrieved from the Internet: <https://www.ncbi.nlm.nih.gov/nuccore/KX118295> (Year: 2024).*
Genbank, KX118298, p. 1 [retrieved on Mar. 29, 2024]. Retrieved from the Internet: <https://www.ncbi.nlm.nih.gov/nuccore/KX118298> (Year: 2024).*
Genbank, KX118297, p. 1 [retrieved on Mar. 29, 2024]. Retrieved from the Internet: <https://www.ncbi.nlm.nih.gov/nuccore/KX118297> (Year: 2024).*

(Continued)

Primary Examiner — Thea D'Ambrosio
Assistant Examiner — Lioubov G Korotchkina
(74) Attorney, Agent, or Firm — LUCAS & MERCANTI, LLP

(57) ABSTRACT

Three recombinant E. coli strains produce the enzymes CPD-photolyase, 6,4-bifunctional photolyase and 6,4-photolyase, from bacterial Antarctic isolates of the genus Hymenobacter the first one and Sphingomonas the others. It is also disclosed a process of production and purification of the recombinant enzymes with high performance, high degree of purity and high catalytic repair activity, having applications in, but it is not limited to, cosmetics and pharmaceutical industry. A fast, cheap and qualitative method is provided for the determination of the CPD photolyase activity.

Figure 1:
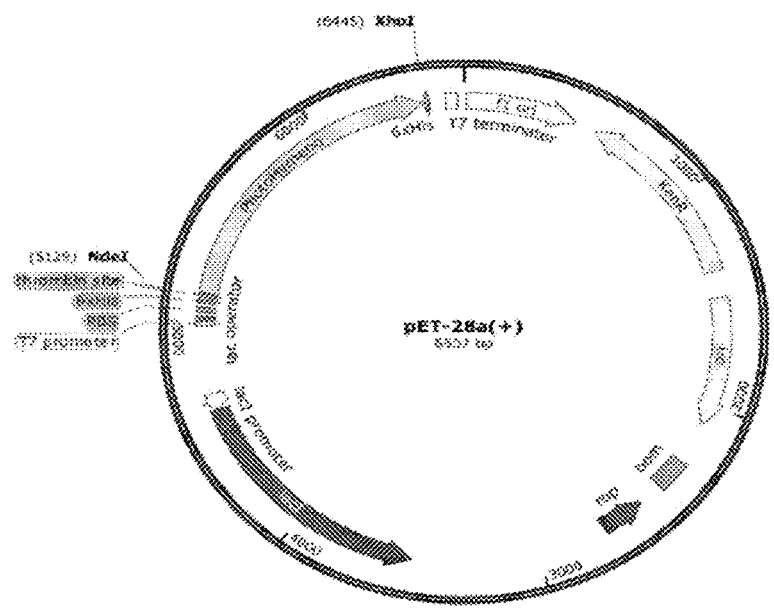

8 Claims, 5 Drawing Sheets
Specification includes a Sequence Listing.

(56) References Cited

OTHER PUBLICATIONS

Zhong, D., "Electron Transfer Mechanisms of DNA Repair by Photolyase," Annual Review of Physical Chemistry, 2015, 66:69-715, Annual Reviews Inc., United States. (28 pages).

Stege, H. et al., "Enzyme plus light therapy to repair DNA damage in ultraviolet-B-irradiated human skin," PNAS, 2000, 97:1790-1795, United States (6 pages).

Berardesca, Enzo et al., "Reduced ultraviolet-induced DNA damage and apoptosis in human skin with topical application of a photolyase-containing DNA repair enzyme cream: Clues to skin cancer prevention," Molecular Medicine Reports, 2012, 5:570-574, Spandidos Publications, Greece (5 pages).

Puig-Butillé et al., Role of CPI-17 in restoring skin homoeostasis in cutaneous field of cancerization: effects of topical application of a film-forming medical device containing photolyase and UV filters, Experimental Dermatology, 2013, 22:494-496, Wiley-Blackwell Publishing Ltd., United Kingdom (3 pages).

Stewart, Ian et al., "Recreational and occupational field exposure to freshwater cyanobacteria—a review of anecdotal and case reports, epidemiological studies and the challenges for epidemiologic Assessment," Environmental Health: A Global Access Science Source 2006, 5:6, 24, BioMed Central Ltd., United Kingdom (13 pages).

Albarracín, Virginia Helena et al., "Forged Under the Sun: Life and Art of Extremophiles from Andean Lakes," Photochemistry and Photobiology Journal, 2016, 92: 14-28, John Wiley & Sons Ltd. (15 pages).

Dai, Jun et al., "*Hymenobacter tibetensis* sp. nov., a UV-resistantbacteriumisolated from Qinghai-Tibet plateau," Systematic and AppliedMicrobiology, 2009, 32: 543-548, Urban and Fischer Verlag Jena, Netherlands (6 pages).

Su, Shiyou et al., "Hymenobacter kanuolensis sp. nov., a novel radiation-resistant bacterium," International Journal of Systematic and Evolutionary Microbiology, 2014, 64, 2108-2112, Microbioloty Society, United Kingdom(6 pages).

Mageswaria, Anbazhagan et al., "Astaxanthin from psychrotrophic Sphingomonas faeni exhibits antagonism against food-spoilage bacteria at low temperatures," Microbiological Research, 2015, 179: 38-44, Urban and Fischer Verlag Jena, Netherlands (7 pages).

Marizcurrena, Juan Jose et al., "Searching for novel photolyases in UVC-resistant Antarctic bacteria," Extremophiles, 2017, 21:409-418, Springer Japan, Germany (10 pages).

Studier, F. William, "Protein production by auto-induction in high-density shaking cultures," Protein Expression and Purification, 2005, 41:207-234, Academic Press Inc., United States (28 pages).

Sambrook et al., "Molecular Cloning: A Laboratory Manual," 1989, Paginas, 3, $2^{nd}$ edition, CSH Laboratory Press, Cold Spring Harbor, NY (11 pages).

Lee, Jae-Jin et al., "*Hymenobacter sedentarius* sp. nov., isolated from a soil," Journal of Microbiology, 2016, vol. 54, No. 4, pp. 283-289 (7 pages).

\* cited by examiner

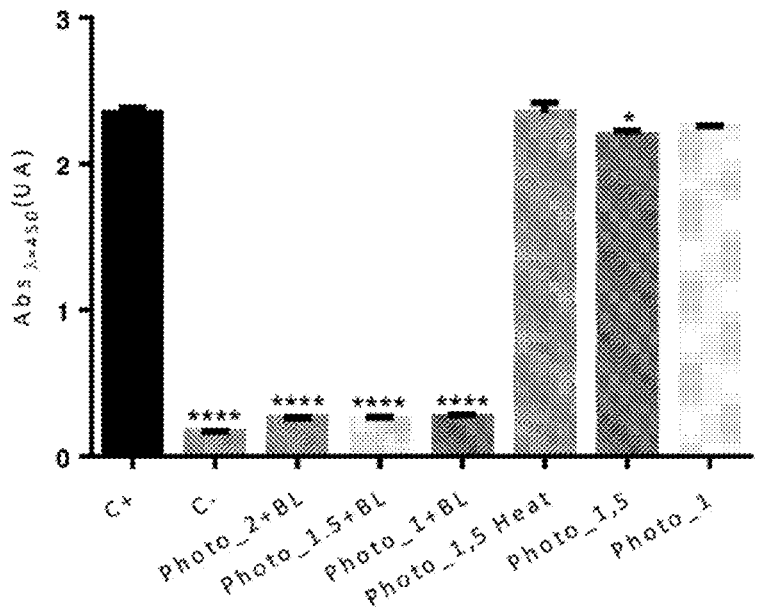

Figure 7

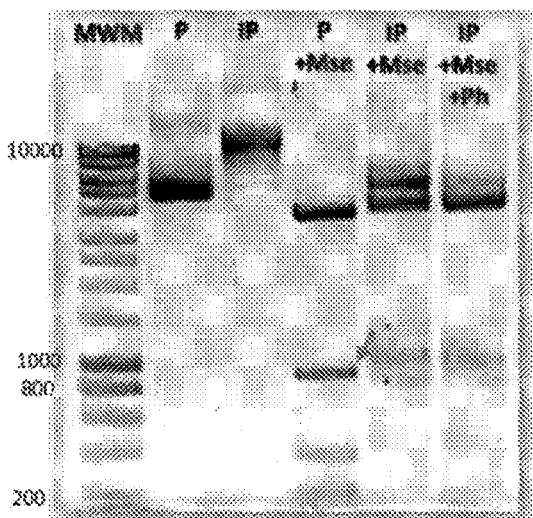

Abbreviations are as follows (from left to right): MWM, molecular weight marker; P, plasmid pUC18-2; IP, UVC-irradiated pUC18-2; P + Mse, pUC18-2 digested with the MseI restriction enzyme; IP + Mse, UVC-irradiated pUC18-2 digested with the MseI restriction enzyme; IP + Mse + Ph, UVC-irradiated pUC18-2 is incubated with the UV11 CPD-photolyase and digested with the MseI restriction enzyme. The arrow points to the miniTn5 DNA fragment realized by the MseI restriction enzyme.

Figure 8

Abbreviations are as follows: C-, non-irradiated calf thymus DNA (non-damaged DNA); C+, 10 Joules UVC-irradiated DNA (damaged DNA); 6,4, DNA samples treated with the recombinant 6,4-photolyase at a concentration of 2 mg/ml, as described above.

SEQUENCE LISTING

<160> NUMBER OF SEQ ID NOS: 6

<210> SEQ ID NO 1
<211> LENGTH: 1314
<212> TYPE: DNA
<213> ORGANISM: Artificial Sequence
<220> FEATURE:
<223> OTHER INFORMATION: CPD-photolyase from Hymenobacter sp. UV11

<400> SEQUENCE: 1

| | | | | | |
|---|---|---|---|---|---|
| atgaagatta | ccctgttctg | gcaccgtcgt | gacctgcgtt | tccaagacaa | tgcgggcctg | 60 |
| gcggcggcgc | tgcaaagcag | ccatccggtg | ctgccgctgt | ttatctacga | ccagaccatt | 120 |
| ctggagaagc | tgccgaaaga | cgatgcgcgt | ctgaccttca | tctttgatca | agtggaacgt | 180 |
| ctggcgcatg | aggcgcatga | agcgggtggc | ggtctgctgg | cgcgttatgg | tcacaccccg | 240 |
| gacgttttca | acagctgct | gaaggactac | gatgtggcgg | cggtttatac | caacgaggac | 300 |
| tacgaaccgt | atgcgaccga | gcgtgatacc | gcgatcgcga | aactgctgga | aaagaacgac | 360 |
| gttgcgttca | gagctttaa | agatcaagtg | attttcgcga | aggaagaggt | gctgaccaag | 420 |
| aacggcaaac | gagcaaggt | gtttggtgcg | tacagcaaag | cgtggcaagc | gaaggttacc | 480 |
| ccggacgatt | tcaagccgca | cccgagcagc | cgtctgctga | agaaagagaa | cctggcgctg | 540 |
| ccgcaccgtg | cggacgcgaa | acgtccggat | ctggagagca | tgggttttgt | tcgtcatgaa | 600 |
| cagtggaccc | cgccggcgca | cctgccgccg | gcggaagtgg | ttaaacgtta | tgacaaggtt | 660 |
| cgtgatctgc | cggcggaaaa | acgtggcacc | accgtatga | gcgtgcacct | gcgttttggt | 720 |
| accgttagca | tccgtcagct | gatgcagcaa | gcgcaagagc | tgaacaacaa | gctgctgaac | 780 |
| gaaatgattt | ggcgtgactt | ctttatgatg | ctgctgtggc | acttcccgaa | caccgcgacc | 840 |
| gaagcgtacg | atccgaaaat | gcgtcacctg | ccgtaccgtg | acgatccgga | gcaatatcgt | 900 |
| gcgtggtgcg | aaggccgtac | cggttacccg | ctggttgacg | cgggcatgcg | tcagctgaac | 960 |
| caaaccggtt | atatgcataa | ccgtgcgcgt | attgcggcgg | cgggcttcct | ggttaagcag | 1020 |
| ctgtttattg | attggaccct | gggcgagcac | tacttcagcg | aaaaactgct | ggactatgat | 1080 |
| atgagcaaca | acgtgggcaa | ctggcaatgg | atggcgggta | ccggtgcggt | ggcggcgccg | 1140 |
| tggtttcgtg | tttacagccc | ggacagccag | caaaaacagt | atgatccgga | gtacgcgtat | 1200 |
| gtgaagcaat | gggttccgga | attcggtacc | gacaaatacc | cggcgccgat | tgttgaccac | 1260 |
| aagttcggtc | gtgagcgtgc | gattgatctg | attcgtaaag | gccgtaccaa | gtaa | 1314 |

<210> SEQ ID NO 2
<211> LENGTH: 437
<212> TYPE: PRT
<213> ORGANISM: Artificial Sequence
<220> FEATURE:
<223> OTHER INFORMATION: CPD-photolyase protein sequence

<400> SEQUENCE: 2

Met Lys Ile Thr Leu Phe Trp His Arg Arg Asp Leu Arg Phe Gln Asp
1               5                   10                  15

Asn Ala Gly Leu Ala Ala Ala Leu Gln Ser Ser His Pro Val Leu Pro
            20                  25                  30

Leu Phe Ile Tyr Asp Gln Thr Ile Leu Glu Lys Leu Pro Lys Asp Asp
        35                  40                  45

Ala Arg Leu Thr Phe Ile Phe Asp Gln Val Glu Arg Leu Ala His Glu
    50                  55                  60

Ala His Glu Ala Gly Gly Gly Leu Leu Ala Arg Tyr Gly His Thr Pro

```
            65                  70                  75                  80
        Asp Val Phe Lys Gln Leu Leu Lys Asp Tyr Asp Val Ala Ala Val Tyr
                        85                  90                  95

Thr Asn Glu Asp Tyr Glu Pro Tyr Ala Thr Glu Arg Asp Thr Ala Ile
                        100                 105                 110

Ala Lys Leu Leu Glu Lys Asn Asp Val Ala Phe Lys Ser Phe Lys Asp
                        115                 120                 125

Gln Val Ile Phe Ala Lys Glu Val Leu Thr Lys Asn Gly Lys Pro
                        130                 135                 140

Ser Lys Val Phe Gly Ala Tyr Ser Lys Ala Trp Gln Ala Lys Val Thr
        145                 150                 155                 160

Pro Asp Asp Phe Lys Pro His Pro Ser Ser Arg Leu Leu Lys Lys Glu
                        165                 170                 175

Asn Leu Ala Leu Pro His Arg Ala Asp Ala Lys Arg Pro Asp Leu Glu
                        180                 185                 190

Ser Met Gly Phe Val Arg His Glu Gln Trp Thr Pro Ala His Leu
                        195                 200                 205

Pro Pro Ala Glu Val Val Lys Arg Tyr Asp Lys Val Arg Asp Leu Pro
        210                 215                 220

Ala Glu Lys Arg Gly Thr Thr Arg Met Ser Val His Leu Arg Phe Gly
        225                 230                 235                 240

Thr Val Ser Ile Arg Gln Leu Met Gln Gln Ala Gln Glu Leu Asn Asn
                        245                 250                 255

Lys Leu Leu Asn Glu Met Ile Trp Arg Asp Phe Phe Met Met Leu Leu
                        260                 265                 270

Trp His Phe Pro Asn Thr Ala Thr Glu Ala Tyr Asp Pro Lys Met Arg
                        275                 280                 285

His Leu Pro Tyr Arg Asp Asp Pro Glu Gln Tyr Arg Ala Trp Cys Glu
                        290                 295                 300

Gly Arg Thr Gly Tyr Pro Leu Val Asp Ala Gly Met Arg Gln Leu Asn
        305                 310                 315                 320

Gln Thr Gly Tyr Met His Asn Arg Ala Arg Ile Ala Ala Ala Gly Phe
                        325                 330                 335

Leu Val Lys Gln Leu Phe Ile Asp Trp Thr Leu Gly Glu His Tyr Phe
                        340                 345                 350

Ser Glu Lys Leu Leu Asp Tyr Asp Met Ser Asn Asn Val Gly Asn Trp
                        355                 360                 365

Gln Trp Met Ala Gly Thr Gly Ala Val Ala Pro Trp Phe Arg Val
                        370                 375                 380

Tyr Ser Pro Asp Ser Gln Gln Lys Gln Tyr Asp Pro Glu Tyr Ala Tyr
        385                 390                 395                 400

Val Lys Gln Trp Val Pro Glu Phe Gly Thr Asp Lys Tyr Pro Ala Pro
                        405                 410                 415

Ile Val Asp His Lys Phe Gly Arg Glu Arg Ala Ile Asp Leu Ile Arg
                        420                 425                 430

Lys Gly Arg Thr Lys
                        435

<210> SEQ ID NO 3
<211> LENGTH: 1488
<212> TYPE: DNA
<213> ORGANISM: Artificial Sequence
<220> FEATURE:
<223> OTHER INFORMATION: 6,4-bifunctional photolyase from Sphingomonas
      sp UV9
```

<400> SEQUENCE: 3

```
atgccggcga tcctgccgca cagcctgagc agctggagcg aggcgccgcg tgtgcgtgcg      60
ctgaacgcgc gtgatgtgcg tccggacggt cgttacgttc tgtgctggct gcagcaagcg     120
ctgcgtgcgc gtgataaccc ggttatcgac gcggcgatte atctgggtaa cgcgctgggt     180
ctgccggtga tcgtttatca cggcctgcgt gaggattacc cgtatgcgag cgaccgtctg     240
caccgttttta ttctgggtgc gagccgtgac ctggcgcgtg aatgccgtca gcgtggcctg    300
gcgtgcgtgc aatacgttga tcgtgcggac gcgcgtgaga agggtctggt gtatcgtctg     360
gcggcggata cgcggcggt gctggttgaa gaccagccga ccttcgttgc gcgttggcaa      420
agcgagcgtt tgcggcgcg tatcgaacgt gcggtgttcg cggttaacgc ggcgtgcctg      480
gtgccgccgg cggttctggg cgatggtatt ggcagcacca ccgcgttccg tcgtcgtcac     540
cagccggtgc gtagcgattg caagaaacc accgatgcgg cgccggcggt tgcgccgtac      600
gatggtccgc tgccgtatac cccggaccgt ctggaagcgt gcagcgacac cgatctggac    660
cacctggttg cgaccgcggc gattgaccac accctgccgg ttagcaccat gtttccggcg    720
ggtcgtgagg tgcgctggt gcacctggaa cgtctgatgg ataccgttct gccgacctac     780
gcggcgaccc gtaacgatgc gaccaacccg gtgggtgcga gcatgctgag cccgtatctg    840
cacttcggtg ttattggccc gcgtgatgtg atggcgaccg ttgaggcggc ggatgcgccg    900
gcggcgagca aggagaaatt tgcggatgaa ctgctgacct ggcgtgaatg gttccactat   960
caagcgcgta ccctgccggc gccggagcgt tatgaccgta tcgcggaatg ggcgcaagaa   1020
accctggaag cgcatgcggt ggatccgcgt ccggacattg aaaccctggc ggcgctgctg   1080
catggcgaga cccgtgatga acctggaac gcgtgccagc gtcaatttct gatcgacggt    1140
tggatgcaca acaacctgcg tatgtactgg ggcaaacgta tcattgcgat gaccccggat   1200
ccgcagaccg cgtgggcgac cgcgtgctac ctgaacgacc gtctgagcct ggatggtcgt   1260
gacccgagca cctatggcaa cattgcggcg acctttggtg gcggtagccc gggtcgtgaa   1320
ggtccgagcg tgtacggcaa ggttccgacc cgtagcgatg gcagcacccg tcaccgtccg   1380
ggcggtccgg cgtggctgca cgctgcgcg acccgtagcc gtccggaccc ggcggttccg   1440
agcgatctgc cgaccgacct gtatctggcg ggtaaaagcc cgctgtaa                 1488
```

<210> SEQ ID NO 4
<211> LENGTH: 495
<212> TYPE: PRT
<213> ORGANISM: Artificial Sequence
<220> FEATURE:
<223> OTHER INFORMATION: 6,4-bifunctional photolyase from Sphingomonas sp. UV9

<400> SEQUENCE: 4

```
Met Pro Ala Ile Leu Pro His Ser Leu Ser Ser Trp Ser Glu Ala Pro
1               5                   10                  15

Arg Val Arg Ala Leu Asn Ala Arg Asp Val Arg Pro Asp Gly Arg Tyr
            20                  25                  30

Val Leu Cys Trp Leu Gln Gln Ala Leu Arg Ala Arg Asp Asn Pro Val
        35                  40                  45

Ile Asp Ala Ala Ile His Leu Gly Asn Ala Leu Gly Leu Pro Val Ile
    50                  55                  60

Val Tyr His Gly Leu Arg Glu Asp Tyr Pro Tyr Ala Ser Asp Arg Leu
65                  70                  75                  80
```

```
His Arg Phe Ile Leu Gly Ala Ser Arg Asp Leu Ala Arg Glu Cys Arg
                85                  90                  95
Gln Arg Gly Leu Ala Cys Val Gln Tyr Val Asp Arg Ala Asp Ala Arg
            100                 105                 110
Glu Lys Gly Leu Val Tyr Arg Leu Ala Ala Asp Ser Ala Ala Val Leu
        115                 120                 125
Val Glu Asp Gln Pro Thr Phe Val Ala Arg Trp Gln Ser Glu Arg Phe
130                 135                 140
Ala Ala Arg Ile Glu Arg Ala Val Phe Ala Val Asn Ala Ala Cys Leu
145                 150                 155                 160
Val Pro Pro Ala Val Leu Gly Asp Gly Ile Gly Ser Thr Thr Ala Phe
                165                 170                 175
Arg Arg Arg His Gln Pro Val Arg Ser Asp Trp Gln Glu Thr Thr Asp
            180                 185                 190
Ala Ala Pro Ala Val Ala Pro Tyr Asp Gly Pro Leu Pro Tyr Thr Pro
        195                 200                 205
Asp Arg Leu Glu Ala Cys Ser Asp Thr Asp Leu Asp His Leu Val Ala
210                 215                 220
Thr Ala Ala Ile Asp His Thr Leu Pro Val Ser Thr Met Phe Pro Ala
225                 230                 235                 240
Gly Arg Glu Gly Ala Leu Val His Leu Glu Arg Leu Met Asp Thr Val
                245                 250                 255
Leu Pro Thr Tyr Ala Ala Thr Arg Asn Asp Ala Thr Asn Pro Val Gly
            260                 265                 270
Ala Ser Met Leu Ser Pro Tyr Leu His Phe Gly Val Ile Gly Pro Arg
        275                 280                 285
Asp Val Met Ala Thr Val Glu Ala Ala Asp Ala Pro Ala Ala Ser Lys
290                 295                 300
Glu Lys Phe Ala Asp Glu Leu Leu Thr Trp Arg Glu Trp Phe His Tyr
305                 310                 315                 320
Gln Ala Arg Thr Leu Pro Ala Pro Glu Arg Tyr Asp Arg Ile Ala Glu
                325                 330                 335
Trp Ala Gln Glu Thr Leu Glu Ala His Ala Val Asp Pro Arg Pro Asp
            340                 345                 350
Ile Glu Thr Leu Ala Ala Leu Leu His Gly Glu Thr Arg Asp Glu Thr
        355                 360                 365
Trp Asn Ala Cys Gln Arg Gln Phe Leu Ile Asp Gly Trp Met His Asn
370                 375                 380
Asn Leu Arg Met Tyr Trp Gly Lys Arg Ile Ile Ala Met Thr Pro Asp
385                 390                 395                 400
Pro Gln Thr Ala Trp Ala Thr Ala Cys Tyr Leu Asn Asp Arg Leu Ser
                405                 410                 415
Leu Asp Gly Arg Asp Pro Ser Thr Tyr Gly Asn Ile Ala Ala Thr Phe
            420                 425                 430
Gly Gly Gly Ser Pro Gly Arg Glu Gly Pro Ser Val Tyr Gly Lys Val
        435                 440                 445
Pro Thr Arg Ser Asp Gly Ser Thr Arg His Arg Pro Gly Gly Pro Ala
450                 455                 460
Trp Leu His Ala Ala Thr Arg Ser Arg Pro Asp Pro Ala Val Pro
465                 470                 475                 480
Ser Asp Leu Pro Thr Asp Leu Tyr Leu Ala Gly Lys Ser Pro Leu
                485                 490                 495
```

<210> SEQ ID NO 5
<211> LENGTH: 1551
<212> TYPE: DNA
<213> ORGANISM: Artificial Sequence
<220> FEATURE:
<223> OTHER INFORMATION: 6,4-photolyase from Sphingomonas sp UV9

<400> SEQUENCE: 5

```
atgaccatta ccaccctggt tccgattctg ggcgatcaac tgaccattga cctggcgagc        60
ctgcgtgacc gtgacccggc gaccaccatc gtgctgatga tggaagtggc ggacgaaacc       120
acctatgttc gtcaccacaa gcgtaaaatc gcgtacattc tgagcgcgat gcgtcaccat       180
gcggaggcgc tgcgtgcggc gggttggacc gttgaataca cccgtctgga cgatccggac       240
aacgcgggta gctttaccgg tgaaattgcg cgtgcggtgg agcgtcatga tccggaacgt       300
attgtggtta ccgagggtgg cgaatggcgt gtgatggcga tgctggagag ctgggaaacc       360
ctgttcggta tcccggttgc gattcgtagc gacgatcgtt tcctggcgag ccacgcggac       420
tttgaaacct gggcggcgga gcgtaagagc ctgaccatgg aatggtttta tcgtcagatg       480
cgtacccgta ccggcctgct gatgaccgac ggcaagccgg agggcgaccg ttggaacttc       540
gataaagaaa accgtaagcc ggcgaaaaac gatctgctga tgccgcgtcc gctggttttt       600
gcgccggacg cgatcaccca agatgtgctg gcgctggttg cggaccgttt cgcggatcac       660
ccgggtagcc tggacggctt tgattacgcg gttaccgcgc cggatgcgga gcgtcaggcg       720
gcgaacttct ttcgtcacgc gctgcgtcaa ttcggtgact atgaggatgc gatgctgacc       780
ggcgaacgtc acctgtggca cagcatcctg agcccgtaca ttaacagcgg tctgctggac       840
ccgctggatc tgtgccgtcg tgcggaggcg gaatatcgtg cgggtcgtgc gccgctgaac       900
gcggttgagg ttacatccg tcagatcatt ggctggcgtg aatatatgcg tggtatttac       960
tggcgtgagg gcccggacta tgtggaacgt aactttctgg atcaccaccg tgagctgccg      1020
ggttggtact ggaccggcga aaccgacatg cactgcctgc gtgaggcgat cggtcagacc      1080
ctggaaaccg cgcacgcgca ccacattcaa cgtctgatgg tgaccggtaa ctttgcgctg      1140
ctgattggtg cggaccccgg cgaaggttca caaatggtacc tggaagtgta tgttgatgcg      1200
tacgagtggg tggaactgcc gaacaccctg ggtatgagcc agtttggcga cggtggcctg      1260
ctgggtagca aaccgtatat cagcagcggc gcgtacattg accgtatgag cgattattgc      1320
ggccagtgcc gttacaaggt gaaacaacgt attggtccgg atgcgtgccc gttcaacgcg      1380
ctgtattggg actttctggc gcgtcacgag gataagctgg gtcgtaacaa ccgtctggcg      1440
atgccgtacc gtaactggca caaacaaacc gaagcggacc gtgatgcgac ccgtgcgcaa      1500
gcggcgggtt ttctggcgag cctggacgcg agcggtgaag cgggttacta a              1551
```

<210> SEQ ID NO 6
<211> LENGTH: 516
<212> TYPE: PRT
<213> ORGANISM: Artificial Sequence
<220> FEATURE:
<223> OTHER INFORMATION: 6,4-photolyase from Sphingomonas sp. UV9

<400> SEQUENCE: 6

```
Met Thr Ile Thr Thr Leu Val Pro Ile Leu Gly Asp Gln Leu Thr Ile
1               5                   10                  15

Asp Leu Ala Ser Leu Arg Asp Arg Asp Pro Ala Thr Thr Ile Val Leu
            20                  25                  30

Met Met Glu Val Ala Asp Glu Thr Thr Tyr Val Arg His His Lys Arg
        35                  40                  45
```

```
Lys Ile Ala Tyr Ile Leu Ser Ala Met Arg His His Ala Glu Ala Leu
 50                  55                  60

Arg Ala Ala Gly Trp Thr Val Glu Tyr Thr Arg Leu Asp Asp Pro Asp
 65                  70                  75                  80

Asn Ala Gly Ser Phe Thr Gly Glu Ile Ala Arg Ala Val Glu Arg His
                 85                  90                  95

Asp Pro Glu Arg Ile Val Val Thr Glu Gly Glu Trp Arg Val Met
                100                 105                 110

Ala Met Leu Glu Ser Trp Glu Thr Leu Phe Gly Ile Pro Val Ala Ile
                115                 120                 125

Arg Ser Asp Asp Arg Phe Leu Ala Ser His Ala Asp Phe Glu Thr Trp
130                 135                 140

Ala Ala Glu Arg Lys Ser Leu Thr Met Glu Trp Phe Tyr Arg Gln Met
145                 150                 155                 160

Arg Thr Arg Thr Gly Leu Leu Met Thr Asp Gly Lys Pro Glu Gly Asp
                165                 170                 175

Arg Trp Asn Phe Asp Lys Glu Asn Arg Lys Pro Ala Lys Asn Asp Leu
                180                 185                 190

Leu Met Pro Arg Pro Leu Val Phe Ala Pro Asp Ala Ile Thr Gln Asp
                195                 200                 205

Val Leu Ala Leu Val Ala Asp Arg Phe Ala Asp His Pro Gly Ser Leu
210                 215                 220

Asp Gly Phe Asp Tyr Ala Val Thr Ala Pro Asp Ala Glu Arg Gln Ala
225                 230                 235                 240

Ala Asn Phe Phe Arg His Ala Leu Arg Gln Phe Gly Asp Tyr Glu Asp
                245                 250                 255

Ala Met Leu Thr Gly Glu Arg His Leu Trp His Ser Ile Leu Ser Pro
                260                 265                 270

Tyr Ile Asn Ser Gly Leu Leu Asp Pro Leu Asp Leu Cys Arg Arg Ala
                275                 280                 285

Glu Ala Glu Tyr Arg Ala Gly Arg Ala Pro Leu Asn Ala Val Glu Gly
                290                 295                 300

Tyr Ile Arg Gln Ile Ile Gly Trp Arg Glu Tyr Met Arg Gly Ile Tyr
305                 310                 315                 320

Trp Arg Glu Gly Pro Asp Tyr Val Glu Arg Asn Phe Leu Asp His His
                325                 330                 335

Arg Glu Leu Pro Gly Trp Tyr Trp Thr Gly Glu Thr Asp Met His Cys
                340                 345                 350

Leu Arg Glu Ala Ile Gly Gln Thr Leu Glu Thr Ala His Ala His His
                355                 360                 365

Ile Gln Arg Leu Met Val Thr Gly Asn Phe Ala Leu Leu Ile Gly Ala
                370                 375                 380

Asp Pro Ala Lys Val His Lys Trp Tyr Leu Glu Val Tyr Val Asp Ala
385                 390                 395                 400

Tyr Glu Trp Val Glu Leu Pro Asn Thr Leu Gly Met Ser Gln Phe Gly
                405                 410                 415

Asp Gly Gly Leu Leu Gly Ser Lys Pro Tyr Ile Ser Ser Gly Ala Tyr
                420                 425                 430

Ile Asp Arg Met Ser Asp Tyr Cys Gly Gln Cys Arg Tyr Lys Val Lys
                435                 440                 445

Gln Arg Ile Gly Pro Asp Ala Cys Pro Phe Asn Ala Leu Tyr Trp Asp
450                 455                 460
```

```
Phe Leu Ala Arg His Glu Asp Lys Leu Gly Arg Asn Asn Arg Leu Ala
465                 470                 475                 480

Met Pro Tyr Arg Asn Trp His Lys Gln Thr Glu Ala Asp Arg Asp Ala
                485                 490                 495

Thr Arg Ala Gln Ala Ala Gly Phe Leu Ala Ser Leu Asp Ala Ser Gly
            500                 505                 510

Glu Ala Gly Tyr
        515
```

GENETICALLY MODIFIED BACTERIA PRODUCING THREE DNA REPAIR ENZYMES AND METHOD FOR THE EVALUATION OF DNA REPAIR ACTIVITY

The instant application contains a Sequence Listing which has been submitted electronically in the ASCII text file and is hereby incorporated by reference in its entirety. The ASCII text file is a sequence listing entitled "SUBSTITUTE SEQUENCE LISTING ST25.TXT" created on Jul. 12, 2024 and having a size of 19,331 bytes in compliance of 37 CFR 1.821.

FIELD OF THE INVENTION

The present invention relates to the biotechnology field, molecular biology and the use of recombinant microorganisms for the production of desired compounds. More specifically it describes the production of three photolyases (CPD-photolyase, 6,4-bifunctional photolyase and 6,4-photolyase) by DNA recombinant technology using genes from two Antarctic bacteria. The nucleotide sequences of these genes were optimized for its expression an *Escherichia coli* as host, cloned in an expression vector and transformed to the expression host. The recombinant production and purification of active enzymes were also set up.

The present invention has applications in, but it is not limited to, cosmetics and pharmaceutical industries.

BACKGROUND OF THE INVENTION

Ultraviolet radiation (UV), mainly from sunlight, produces DNA photo-oxidative damage and different lesions such as cyclobutane pyrimidine dimers (CPDs) and pyrimidine (6-4) pyrimidone photoproducts (6,4-photoproducts). When unrepaired, or deficiently repaired, these DNA photoproducts may lead to skin cancer and/or skin photo-aging.

Photolyases (EC 4.1.99.3) are monomeric flavoproteins that enzymatically repair DNA photoproducts (Zhong, D. 2015. Electron transfer mechanisms of DNA repair by photolyase. Annual Review of Physical Chemistry 66: 691-715). The topical application over the human skin of photolyase-containing liposomes provides protection against the DNA damage produced by the exposition to the harmful UV solar radiation, thus preventing cutaneous cancerization and apoptotic cell death (Stege, H. 2000. Enzyme plus light therapy to repair DNA damage in ultraviolet-B-irradiated human skin. Medical Science 97 (4):1790-1795); (Berardesca. 2012. Reduced ultraviolet-induced DNA damage and apoptosis in human skin with topical application of a photolyase-containing DNA repair enzyme cream: clues to skin cancer prevention. Molecular Medicine Reports 5(2):570-4); (Puig-Butillé. 2013. Role of CPI-17 in restoring skin homoeostasis in cutaneous field of cancerization: Effects of topical application of a film-forming medical device containing photolyase and UV filters. Experimental Dermatology 22(7):494-496).

Currently, in the worldwide market some sunscreens include CPD-photolyase encapsulated liposomes from the cyanobacteria *Synechococcus nidulans* (previously known as *Anacystis nidulans*). The *A. nidulans* CPD-photolyase is the only one that has been produced for pharmaceutical and cosmetic uses as liposome-encapsulated photolyase, and currently is directly obtained from plankton extracts. However, when using the photolyase from the *A. nidulans* plankton extract, the cyanobacterial lipopolysaccharides present in the extract might induce various human diseases, such as allergy, or respiratory and skin diseases (Stewart, I. 2006. Recreational and occupational field exposure to freshwater cyanobacteria—a review of anecdotal and case reports, epidemiological studies and the challenges for epidemiologic assessment. Environ Health. 2006 Mar. 24; 5:6). Notwithstanding, some companies offer CPD photolyases from *A. nidulans* produced by recombinant DNA technology using *E. coli*, baculovirus, yeast and mammalian cells as factory cells, although for academic uses. At present, there are no 6,4-photolyases being produced for these uses.

Many documents disclose the use of liposome-encapsulated photolyase from *A. nidulans*, obtained from plankton extract for cosmetic or dermatological uses or from *E. coli* for academic purposes (patents and applications U.S. Ser. No. 10/459,339, EP20080009757, EP20050017347, U.S. Ser. No. 11/399,728), however these inventions inform about the topical cosmetic compositions rather than the production of new photolyases.

Other documents, PT2717907, WO2014011611, KR0180684, US200117060, US2006002884, refer to products or cosmetic treatments with photolyases from other organisms rather than *Hymenobacter* sp. UV11 and *Sphingomonas* sp. UV9, the microorganisms used in this invention.

Likewise, in the documents related to the preparation of liposome with photolyases (CN103212066, CN101144088, CN103212066) or to the preparation of photolyases in recombinant form (CN105087535, CN105062999, CN103966193, WO2014166137, CN1624120) no elements were found that refer to the invention disclosed in this application.

Native microbial Antarctic communities, challenged by a combination of physical stresses including the exposure to UV radiation, probably develop cooperative strategies to cell with. Among mechanisms involved in UV-resistance such as cell protection and tolerance through the production of antioxidant and DNA repair enzymes (Albarracin, V H. 2016. Forged Under the Sun: Life and Art of Extremophiles from Andean Lakes. Photochemistry and Photobiology Journal. 92(1):14-28), being that the DNA repair mechanism involving photolyases is the basis of this application. In particular, *Hymenobacter* and *Sphingomonas* are microbial genera known for their high resistance to UV radiation.

The genus *Hymenobacter* belongs to the phylum Bacteroidetes, order Sphingobacteriales, family Cytophagaceae, comprises 40 recognized species with at least five UV-resistant species: *H. actinosclerus*, *H. xinjiangensis*, *H. tibetensis*, *H. rubidus*, *H. kanuolensis* (Dai, J. 2009. *Hymenobacter tibetensis* sp. nov., a UV-resistant bacterium isolated from Qinghai-Tibet plateau, Systematic and Applied Microbiology-Journal 32 (8):543-8), (Eu, S. 2014. *Hymenobacter kanuolensis* sp. nov., a novel radiation-resistant bacterium. International Journal of Systematic and Evolutionary Microbiology 64 (Pt 6):2108-12).

On the other hand the genus *Sphingomonas*, a member of the family Sphingomonadaceae, order Sphingomonadales, class Alphaproteobacteria contains 89 validly named species, which form pigmented colonies (yellow to orange pigments) with potential applications in medicine (Mageswari, A. 2015, Astaxanthin from psychotropic *Sphingomonas faeni* exhibits antagonism against food-spoilage bacteria at low temperatures. Microbiological Research 179:38-441.

We have found that among our UVC-resistant bacteria (Marizcurrena, J J. 2017. Searching for novel photolyases in UVC-resistant Antarctic bacteria. 21(2):409-418), the bloody-red colony-forming *Hymenobacter* sp. UV11 isolate shows greater resistance to UVC-radiation (63% survival at 300 J m$^{-2}$) as compared to *H. rubidus* strain DG7BT (0.1% survival at 300 J m$^{-2}$) and other *Hymenobacter* strains (Lee, J J. 2016. *Hymenobacter sedentarius* sp. nov., isolated from a soil. Journal of Microbiology 54(4):283-9). Isolate UV11 also shows greater UVC-resistance compared to the orange colony-forming *Sphingomonas* sp. UV9 isolate, the other UVC-resistant bacterium from our bacterial collection.

BRIEF DESCRIPTION OF THE INVENTION

This invention provides three genetically modified bacteria for the production of CPD-photolyase, 6,4-bifunctional photolyase and 6,4-photolyase, each with high performance, high degree of purity and high catalytic activity.

It describes the genetic modifications done on genes from Antarctic bacteria, the expression of the cloned genes for the production of CPD-photolyase, 6,4-bifunctional photolyase and 6,4-photolyase in *Escherichia coli*, the method of purification, as well as a fast, cheap and qualitative method for the determination of the CPD-photolyase activity.

The present invention refers to the development of genetically modified *E. coli* strains that produce CPD-photolyase, 6,4-bifunctional photolyase and 6,4-photolyase from Antarctic bacteria. All three were produced by recombinant DNA technology using *E. coli* as cell factory. CPD-photolyase was produced from a gene identified in *Hymenobacter* sp. UV11 and 6,4-bifunctional photolyase and 6,4-photolyase from genes identified in *Sphingomonas* sp. UV9.

All three genetically modified *E. coli* strains have been deposited in International Depositary Authorities (IDA). *E. coli* strains that produce CPD-photolyase and 6,4-bifunctional photolyase were deposited in Colección Espanola de Cultivos Tipo (CECT) (Parc Cientific Universitat de Valencia, Spain) under the designation of *E. coli* PhotoUV9 and PhotoUV11, respectively. *E. coli* strain producing 6,4-photolyase was deposited in Colección Chilena de Recursos Genéticos Microbianos (CChRGM) (Avenida Vicente Méndez No 515, Chillan, Chile) under the designation of *Escherichia coli* HL21 (Arctic) PhotoSphingo97. Copies of Deposit Certificates are being submitted with this application.

Other objects of this invention are the recombinant production of CPD-photolyase, 6,4-bifunctional photolyase and 6,4-photolyase obtained by the process here described.

The enzymes were easily produced in a low-cost growing host cell as *E. coli* and showed repairing activity of UVC-induced DNA lesions in CHO and HaCat cell lines, but also in calf thymus DNA, where the CPD-photolyase from *Hymenobacter* sp. UV11 showed CPD repair activity on both double and single strand DNA.

We have also shown by immunoassay that the recombinant 6,4-bifunctional photolyase from the bacterial Antarctic isolate *Sphingomonas* sp. UV9 showed both CPD- and 6,4 photoproduct repair activities and that the recombinant 6,4-photolyase from *Sphingomonas* sp UV9 showed 6,4-photoproduct repair activity.

We have found that the combination of recombinant photolyases provided in this invention would allow the repair of 100% of DNA lesions induced by UV radiation.

They present high potential uses in pharmaceutical and cosmetic industries, therefore they may be included in cosmetic creams or sunscreens for DNA repair of lesions induced by UV light as well as for the potential treatment of related diseases. Moreover, the high degree of purity reached after purification would avoid the presence of potential allergenic effects associated with some of the components present in bacterial photolyases currently found in the market.

BRIEF DESCRIPTION OF DRAWINGS AND FIGURES

Table 1—DNA repair assay (Comet assay) using Chinese Hamster Ovary (CHO) cells (experiments carried on with the CPD-photolyase enzyme)

Table 2—DNA repair assay (Comet assay) using immortalized non-tumorigenic human epidermal. (HaCat) cells experiments carried on with the CPD-photolyase enzyme)

Table 3—CPD-repair activity by immunoassay using the CPD-photolyase enzyme from *Hymenobacter* sp. UV11)

Table 4—6,4-photoproduct-repair activity by immunoassay (using the 6,4-bifunctional photolyase, enzyme from *Sphingomonas* sp. UV9)

Table 5—CPD-repair activity by immunoassay (using the 6,4-bifunctional photolyase enzyme, from *Sphingomonas* sp. UV9)

Table 6—6,4-photoproduct-repair activity by immunoassay using the 6,4-photolyase, enzyme from *Sphingomonas* sp. UV9).

FIG. 1—Expression vector for the CPD-photolyase from *Hymenobacter* sp. UV11 (PhotoHymeno-pET 28a(+))

Figure 2:
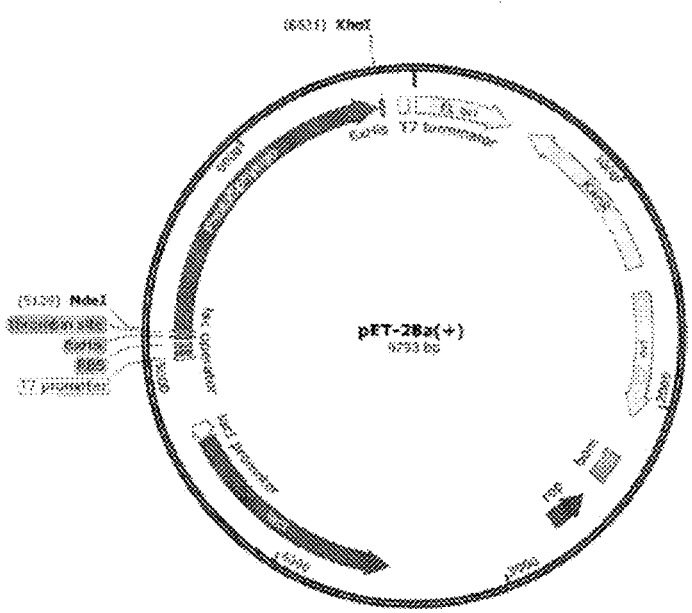

FIG. 2—Expression vector for the 6,4-bifunctional photolyase from *Sphingomonas* sp. UV9 PhotoSphingo-PET 28a(+))

Figure 3:
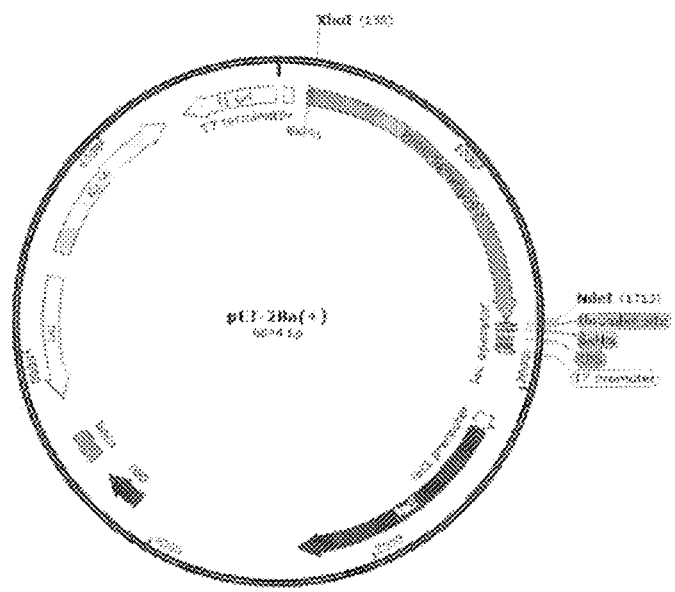

FIG. 3—Expression vector for the 6,4-photolyase from *Sphingomonas* sp. UV9 PhotoSphingo97-pET 28a(+))

Figure 4:
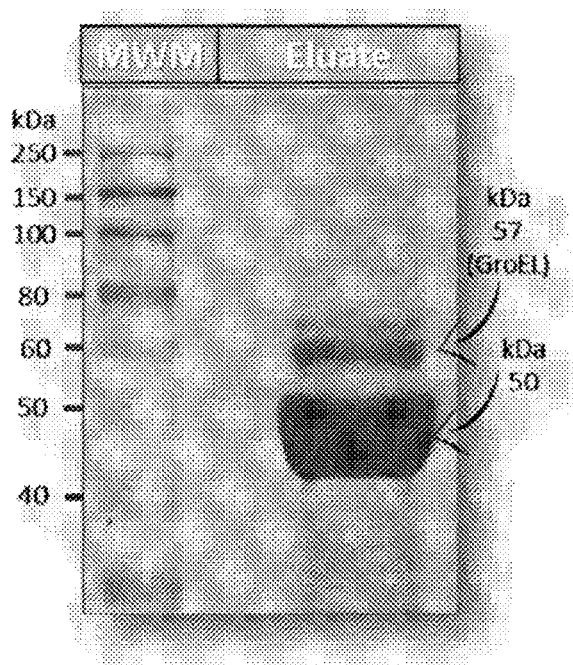

FIG. 4—SDS-PAGE of the 50 kDa molecular weight recombinant CPD-photolyase

Figure 5:
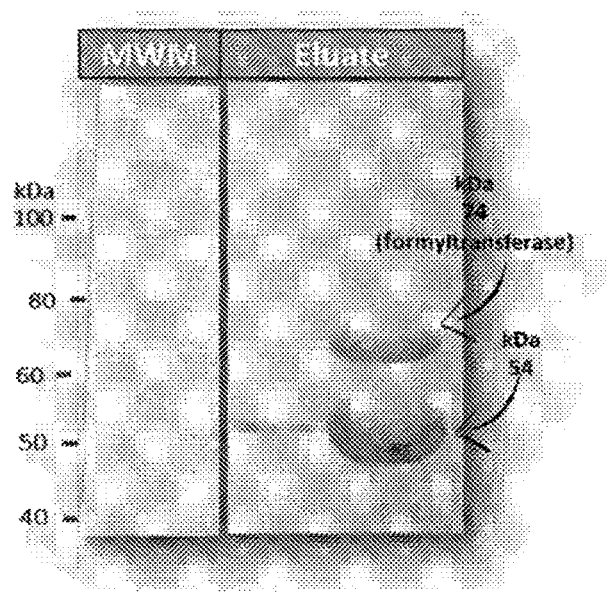
Figure 6:
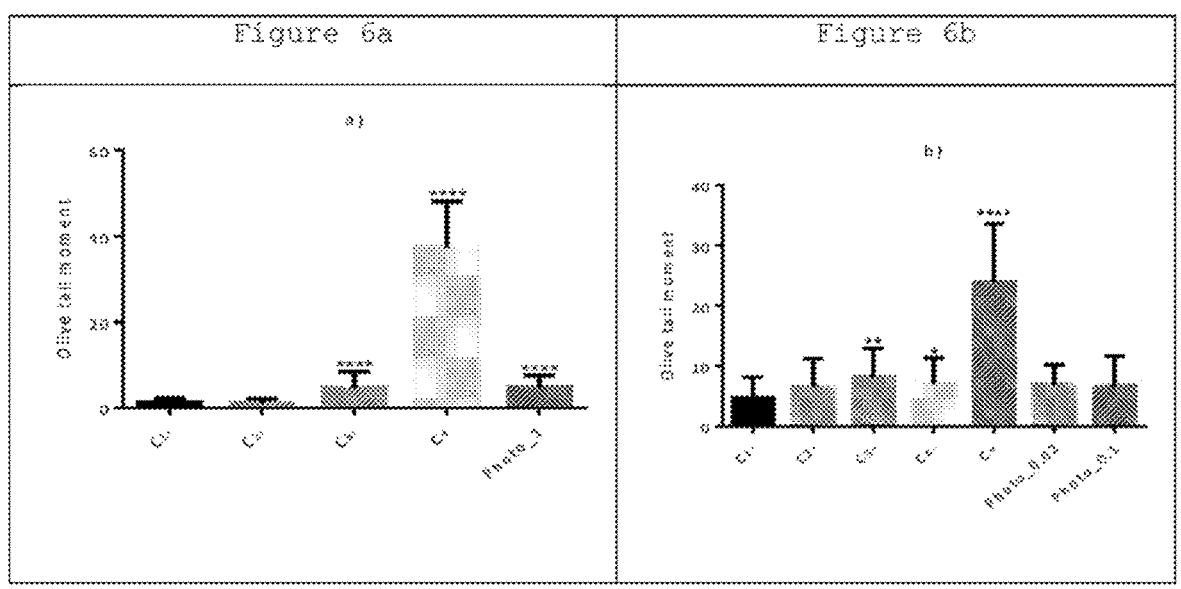

FIG. 5—SDS-PAGE of the 54 kDa molecular weight recombinant 6,4-bi functional photolyase FIG. 6a—Olive tail moment of cells treated with the recombinant CPD-photolyase.

DNA repair assays (Comet assay) using the Chinese Hamster ovary (CHO) cell line.

Asterisks indicate significant difference among treatments (P<0.05).

FIG. 6b—Olive tail moment of cells treated with the recombinant CPD-photolyase. DNA repair assays (Comet assay) using the immortalized non-tumorigenic human epidermal (HaCat) cell line. Asterisks indicate significant difference among treatments (P<0.05).

FIG. 7—CPD-repair activity by immunoassay, carrying out the experiment using recombinant CPD-photolyase and blue light (BL), and under dark conditions or under heat inactivation conditions. Asterisks indicate significant difference among treatments (P<0.05).

FIG. 8. Electrophoretic profile of pUC18-2 under different conditions.

Figure 9:
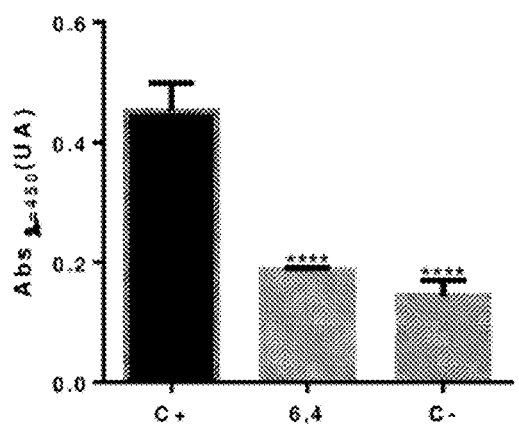

FIG. 9—Column Bars Graph for 6,4-repair activity by immunoassay, carrying out the experiment using recombinant 6,4-photolyase and blue light (BL). Asterisks indicate significant difference among treatments (P<0.05).

DETAILED DESCRIPTION OF THE INVENTION

The present invention provides three recombinant *E. coli* strains for the production of CPD or 6,4, or bifunctional-pholotyases with the following characteristics:

(A) The recombinant production of a CPD-photolyase from a bacterial Antarctic isolate of the genus *Hymenobacter*.

(B) The recombinant production of a 6,4-bifunctional photolyase from a bacterial Antarctic isolate of the genus *Sphingomonas*.

(C) The recombinant production of a 6,4-photolyase from a bacterial Antarctic isolate of the genus *Sphingomonas*.

In addition, the invention provides the method of production and purification with high yield of a CPD-photolyase, a 6,4-bifunctional photolyase and a 6,4-photolyase, with DNA repair activity, and a method for the determination of CPD-photolyase activity.

The invention also provides CPD-photolyase, 6,4-bifunctional photolyase and 6,4-photolyase enzymes from bacterial Antarctic isolates of the genus *Hymenobacter* and *Sphingomonas*, respectively, all three enzymes with high purity and the compositions containing them.

Method for the Production of *E. coli* Recombinant Strains (A) The CPD-photolyase gene sequence was obtained from the draft cenome of *Hymenobacter* sp. UV11, optimized for their expression in *E. coli* BL21 (DE3), and synthesized in the host-vector pET28a(+) (FIG. 1).

(B) The 6,4-bifunctional photolyase gene sequence was obtained from the draft genome of *Sphingomonas* sp. UV9, optimized for their expression in *E. coli* BL21 (DE3), and synthesized in the host-vector pET28a(+) (FIG. 2).

(C) The 6,4-photolyase gene sequence was obtained from the draft genome of *Sphingomonas* sp. UV9, optimized for their expression in *E. coli* BL21 (Arctic), and synthesized in the host-vector pET28a(+) (FIG. 3).

The resulting strains of *Escherichia coli* were called PhotoUV11, deposited at CECT (Number CECT 9643), PhotoUV9, deposited at CECT (Number CECT 9642), and PhotoShingo97, deposited at CChRGM (accession number at the form RO134), respectively. The resulting strains of the invention having accession number CECT 9642 and CECT 9643 were deposited on Jun. 7, 2018 at the International Depositary Authority, Coleccion Espanola de Cultivos Tipo (CECT), Edificio 3 CUE. Parc Cientific Universitat de Valencia Catedratico Agustin Escardino, 9, Paterna (Valencia) Spain 46980. The resulting strain of the invention having accession number CChRGM917 was deposited on Sep. 4, 2019 at the International Depositary Coleccion Chilena de Recursos Geneticos Microbianos (CChRGM), Avenida Vicente Mendez 515, Chillan, Regiog VII, Chile. The deposit was made under the terms of the Budapest Treaty. All restrictions upon public access to the deposit will be irrevocably removed upon the grant of a patent on this application. The deposit will be replaced by Applicant if viable samples cannot be dispensed by the depository.

All three recombinant enzymes, CPD-photolyase, 6,4-bifunctional photolyase and 6,4-photolyase were produced in the auto-inductor Zym-5052 medium and purified by immobilized Metal Affinity Chromatography (IMAC) as active enzymes as shown by Comet Assay (using CHO and HaCat cell lines) (Tables 1 and 2; and Immunochemistry Detection of photoproducts (Tables 3, 4 and 5).

We have also found and demonstrated that the recombinant 6,4-bifunctional photolyase produced by the process here described shows both CPD- and 6,4-photoproduct-repair activities indicating the potential use of this enzyme in the development of new products with pharmaceutical and cosmetic applications.

This invention also describes a simple and fast method to discriminate between active and non-active C2D-photolyases.

The method for the determination of CPD-photolyase activity was developed using a plasmid (pUC18-2) as DNA substrate and can be performed using basic laboratory equipment. This plasmid holds a kanamycin resistance cassette (miniTn5) flanked by TTAA sites (sites of CPD formation). The plasmid (UVC-irradiated and non-irradiated samples) was digested with the MseI restriction enzyme (that recognized TTAA sequences) and subjected to an agarose-gel electrophoresis. When properly UVC irradiated, the TTAA sequences are blocked by the formation of cyclobutane pyrimidine dimers and the MseI enzyme cannot recognize the restriction site and the miniTn5 cassette cannot be released. CPD-activity this was determined by the comparison of the electrophoretic mobility, or restriction pattern, of non-irradiated and UVC-irradiated pUC18-2 samples after the incubation with the CPD-photolyase and further digestion with MseI. Only if the CPDs are repaired by the CPD-photolyase, the miniTn5 cassette was observed as a discrete DNA band in the agarose-gel.

Description of the *E. coli* Developed Strains:

The (A) CPD-photolyase Class I gen from *Hymenobacter* sp. UV11 (GenBank Accession Number KX118295), (B) 6,4-bifunctional photolyase gen from *Sphingomonas* sp. UV9 (GenBank Accession Number KX1182981 and (C) 6,4-photolyase gen from *Sphingomonas* sp. UV9 (GenBank Accession Number KX118297) were modified, synthesized fused in the plasmid vector pET28a(+) (encoding an N-terminal 6-His tag) and transformed into *Escherichia coli* BL21 (DE3) or *Escherichia coli* BL21 (Arctic; cells, using the calcium chloride protocol (Sambrook J., Fritsch E. F., Maniatis T. 1989. Molecular Cloning: A Laboratory Manual, second ed., vol. 3. OSH Laboratory Press, Cold Spring Harbor, NY).

Modifications made to the gene sequences include the change in 20% of the nucleotides. The codon usage was modified by updating the Codon Adaptation Index (CAI) from 0.51 to 0.96 for CPD-photolyase and 6,4-photolyase and from 0.52 to 0.97 for the 6,4-bifunctional photolyase. The GC content was reduced from 61.29% to 56.60%, 65.54% to 59.22% and from 69.06% to 64.27%, respectively.

The constructs (the recombinant plasmid) were synthesized by GenScript (https:www.genscript.com/; USA). The codon optimization for the gene expression in *E. coli* were performed for the CPD-photolyase Class I gene from *Hymenobacter* sp. UV11 (Gen Bank Accession Number KX118295), for the 6,4-bifunctional photolyase gene from *Sphingomonas* sp. UV9 (GenBank Accession Number KX118296) and for the 6,4-photolyase gene from *Sphingomonas* sp. UV9 (GenBank Accession Number KX118297). The optimized genes were fused separately into the plasmid vector pET23a(+) in each case; the expression vectors encode for the production of the photolyases with an N-terminal C-His tag.

For plasmid maintenance, the construct in each case was transformed to *E. coli* DH5α chemo competent cells and inoculated on Luria-Bertoni (LB) plate containing 50 µg/ml of Kanamycin. Plasmids were transformed using the calcium chloride protocol as described by Sambrook et al. 0.1989 (Molecular Cloning: A Laboratory Manual, second ed., vol. 3. CSH Laboratory Press, Cold Spring Harbor, NY Cells were stored in 15% glycerol at −80° C.).

For ax situ microbial repository purpose in an International Depositary Authority (IDA) under the 1977 Budapest treaty on the International Recognition of the deposit of Microorganisms, the recombinant strains were deposited as *Escherichia coli* BL21(DE5) PhotoUV11(A) and PhotoUV9 (B), respectively, in Colección Española Cultivos Tipo (CECT) (parc Cientific Universitat de Valencia, Spain); and *Escherichia coli* BL21 (Arctic) PhotoSphingo97 (C) in Colección Chilena de Fecursos Genéticos Microbianos (CChRGM) (Avenida Vicente Mendez No 515, Chillan, Chile).

For protein production, precultures were obtained by growth on Luria Broth at 37° C. Cells were transferred to the auto-inductor Zym-5052 medium (Studier, F. W. 2005. Protein production by auto-induction in high-density shaking cultures. Protein expression and purification. 41: 207-234), containing 50 µg/ml Kanamycin, and growth at 14° C. and 200 rpm, for 48 h. Cells were harvested, washed twice with PBS (1.37 M calcium chloride, 27 mM potassium chloride, 100 mM sodium dibasic phosphate, 18 mM potassium monobasic phosphate), lysed by sonication (40% Amplitude, at a relative power output of 10) using 50 mM phosphate buffer (supplemented with 50 mM NaCl, at pH and centrifuged twice, first at 7000 g for 10 min at 4° C., and then at 16000 g for 30 min at 4° C.

Photolyases were purified by binding the soluble fraction of proteins at a Ni-NTA affinity resin in binding buffer 150 mM phosphate buffer containing 50 mM NaCl for CPD-photolyase and 6,4-bifunctional. photolyase, and 300 mM NaCl for 6,4-photolyase, supplemented with 50 mM Imidazole for CPD-photolyase and 6,4-bifunctional photolyase, and 10 mM imidazole for 6,4-photolyase) for 1. h at 4° C., washed with binding buffer, eluted with binding buffer containing 250 mM Imidazole and further desalted using Desalting Columns contain Sephadex G-25 resin. All fractions were controlled by SDS-PAGE (FIGS. 4 and 5). Protein concentration was determined by Bradford assay, using bovine serum albumin as standard.

The yield of the process was 42 mg of a 50 kDa protein in 6 ml corresponding to the recombinant CPD-photolyase from *Hymenobacter* sp. UV11 (A) (Protein sequence SEQ ID No 2), 70 mg of a 54 kDa protein in 6 ml corresponding to the 6,4-bifunctional photolyase from *Sphingomonas* sp. UV9 (B) (Protein sequence SEQ ID 4) and 40 mg of a 59 kDa protein in 6 ml corresponding to the 6,4-photolyase from *Sphingomonas* sp. UV9 (C) (Protein sequence SEQ ID 6), each produced from 200 ml culture.

The identity of the recombinant protein was verified by mass spectrometry MALDI/TOFTOF analysis and searching in the NCBI database with peptide m/z values using the MASCOT software.

The activity of the recombinant CPD-photolyase from *Hymenobacter* sp. UV11 was demonstrated in in vitro experiments using comet and immune assays. For comet assay CHO and HaCat cell lines were used (Tables 1 and 2). HaCat or CHO cell samples were washed twice with cold PBS, irradiated with a dose of 4 J m$^{-2}$ UVC radiation (254 nm) using a Spectroline lamp (model ENF-260C/FE), washed again, scraped using a rubber policeman and transferred to eppendorf tubes with 1 ml of PBS. Twenty µl of cell suspension (2×10$^{-6}$ cells) were gently mixed with 80 µl of 1% Low melting-point agarose (LMA), and directly applied to a 1.5% agarose precoated slide. Slides were covered with a coverslip and placed at 4° C. for 5 min. Then, coverslips were removed and slides were submersed in the lysis solution (2.5 M NaCl, 100 mM Na$_2$EDTA, 1 mM Tris buffer at pH 10, 1% Triton X-100) and incubated at 4° C. for 2 h. Slides were washed twice with buffer NET (100 mM NaCl, 10 mM Tris-HCl, 10 mM EDTA; pH 8.0) for 5 min at room temperature. When indicated (treatments with photolyase), 50 µl of recombinant CPD-photolyase at different concentrations (suspended in NET buffer) was applied to the top of gels, irradiated with a UVA lamp (ULTRA-VITALUX OSRAM 300W) for 10 min in a humidity chamber (photoreparation), and then washed twice in buffer: NET. Ail slides (treatments and controls) were loaded with 50 ul of T4 endonuclease V (in buffer NET) (the enzyme cleaves the glycosyl bond of the 5'end of the pyrimidine dimer; unrepaired CPDs are revealed by this enzyme), covered with a coverslip and incubated in a humidified chamber for 30 min at 37° C. DNA fragments were resolved by alkaline-electrophoresis, using the following running buffer: 1 mM Na$_2$EDTA, 0.3 NaOH, at pH 13. DNA was unwinded for 15 min and then, the electrophoresis was performed at 0.7 V/cm, 300 mA for 20 min, in a cold unit at 4° C. The slides were removed and washed in neutralization buffer (0.4 M Tris-HCl; pH 7.5) for 5 min at room temperature, and finally stained with 50 µL ethidium bromide (10 mg/ml). Slides were analyzed using the Computer Program Comet Imager (MetaSystems). At least 50 nuclei per slide were measured (three slides per treatment or control). Three independent biological replicas were performed. CHO (Table 1, FIG. 6a) and HaCat (Table 2, FIG. 6b) cells that were treated with the recombinant CPD-photolyase showed reduced values of olive tall moments, similar to the values found for the control treatments (except for the positive control, UVC-irradiated cells). These results suggest that the recombinant CP-D-photolyase reduced the UVC-DNA damage by approximately 100% of CHO and HaCat cells.

The recombinant CPD-photolyase also showed activity by immunochemistry assay. Immunochemistry of irradiated Calf thymus DNA was performed to quantify CPDs using the High Sensitivity CPD/Cyclobutane Pyrimidine Dimer ELISA kit of CosmoBio (NMMA-K001), with modifications as follows. UVC-irradiated calf thymus DNA. (50 µL of J, 4 µg/ml DNA irradiated with 10 J) was denatured (20 min at 100° C., followed by chilling on ice for 15 min), applied to microtiter wells pre-coated with protamine sulfate and then treated with 150 µL of the recombinant photolyase at different concentrations during 20 min under blue light at room temperature. Experiments were also carried out in darkness conditions. Then, the photolyase was removed by washing with washing buffer, treated with specific monoclonal anti-CPLD antibody clone TDM-2 and washed again. The remaining TDM-2 antibody in each well was then measured by sequential treatment with a secondary biotinylated antibody, streptavidin-peroxidase, and the substrate 3,3',5,5'-tetramethylbenzidine (TMB). The final product develops a color, which was measured at 450 nm. Reactive compounds, including the irradiated calf thymus DNA, antibodies and buffers, were used following manufacturer's instructions (CosmoBio). Results are shown in Table 3 and FIG. 7.

The Immunochemical assay experiments, using commercial antibodies that recognize CPDs, also confirmed that the recombinant CPD-photolyase was purified as an active DNA repairing enzyme. In these experiments, calf-thymus DNA (single stranded DNA) was used as substrate and the recombinant photolyase reduced by 100, the presence of CPDs (UVC-irradiated and non-photolyase treated DNA was considered at an initial damage of 100%). We detected repair activity even by using 1 µg/ml recombinant CPD-photolyase (a 5000-fold dilution of the purified enzyme). When experiments were carried out on darkness, or when the recombinant enzyme was denatured by heat (boiling for 10 min and fast cooling on ice), the repair activity was not detected, discarding false positives or a method artifact. These results support that the recombinant CPD-photolyase from *Hymenobacter* sp. UV11 has been produced as active enzyme, and it needs light for activity. 6,4-photoproducts antibodies were also tested in immunochemical assays, and results suggested that the recombinant CPD-photolyase might not repair this Kind of DNA lesion.

The activity of the recombinant; 6,4-bifunctional photolyase from *Sphingomonas* sp. UV9 was demonstrated in in vitro experiments by using the immunoassay. Both CPD- and 6,4-antibodies were used as described above, reparation the High sensitivity ELISA kit for measuring UV-induced DNA damage from CosmoBio CSR-NM-MA-K004) was used for detecting 6,4-photoproducts. The information (Table 4 and 5) supports that the recombinant 6,4-bifunctional photolyase from *Sphingomonas* sp. UV9 has both CPD- and 6,4-photoproduct repair activities.

The activity of the recombinant 6,4-photolyase from *Sphingomonas* sp. UV9 was demonstrated in in vitro experiments by using the immunoassay. The High sensitivity ELISA kit for measuring UV-induced DNA damage from CosmoBio (CSR-NM-MA-K004), using the 6,4-antibodies, was used. The information (Table 6 and FIG. 9) supports that the recombinant 6,4-photolyase from *Sphingomonas* sp. UV9 has 6,4-photoproduct repair activity.

Finally, the recombinant photolyases were stored in PBS buffer supplemented with 50% glycerol at −80° C. and remained 100% active at least after one-year storage in this conditions.

EXAMPLES

Example 1—DNA Repair Assay (Comet Assay) Using Chinese Hamster Ovary Cells

Olive tail moments and statistics. Experiments were performed using the Chinese Hamster Ovary (CHO) cell line.

It was observed that UVC-irradiated CHO cells that were treated with the recombinant photolyase in the presence of blue light had a significantly lower value of olive tail moment rather than non-photolyase treated cells, suggesting that under the assay conditions the recombinant CPD-photolyase from *Hymenobacter* sp. UV11 reduced the UVC-DNA damage of CHO cells. This photolyase almost completely repaired the DNA damage caused by UVC radiation.

These results were supported by the statistic test (multiple comparison ANOVA assay), where 50 comets per treatment were counted in duplicate.

TABLE 1

| Test details | Mean 1 | Mean 2 | Mean Difference | Standard error for the difference | Significance | Summary |
|---|---|---|---|---|---|---|
| $C_1$- vs. $C_2$- | 1.321 | 1.132 | 0.189 | 0.6291 | No | ns |
| $C_1$- vs. $C_3$- | 1.321 | 4.838 | −3.517 | 0.7705 | Yes | **** |
| $C_1$- vs. C+ | 1.321 | 37.27 | −35.95 | 0.7705 | Yes | **** |
| $C_1$- vs. Photo_1 | 1.321 | 4.869 | −3.548 | 0.7121 | Yes | **** |
| $C_2$- vs. $C_3$- | 1.132 | 4.838 | −3.706 | 0.7705 | Yes | **** |
| $C_2$- vs. C+ | 1.132 | 37.27 | −36.14 | 0.7705 | Yes | **** |
| C2- vs. Photo_1 | 1.132 | 4.869 | −3.737 | 0.7121 | Yes | **** |
| $C_3$- vs. C+ | 4.838 | 37.27 | −32.44 | 0.8897 | Yes | **** |
| $C_3$- vs. Photo_1 | 4.838 | 4.869 | −0.031 | 0.8396 | No | ns |
| C+ vs. Photo_1 | 37.27 | 4.869 | 32.4 | 0.8396 | Yes | **** |

Abbreviations are as follows: C1−, non-irradiated cells (non-damaged DNA); C2−, non-irradiated cells treated with endonuclease T4 V (basal DNA damage under normal conditions); C3−, UVC-irradiated cells (damaged DNA); C4−, non-irradiated cells treated with the recombinant photolyase (potential damage 5 produced by the recombinant photolyase); C+, UVC-irradiated cells treated with endonuclease T4 V (total damage of DNA); Photo_1, Photo_0.1 and Photo_0.02 are cells treated with 50 µl of 1, 0.1 and 0.02 mg/ml recombinant CPD photolyase.

Example 2—DNA Repair Assay (Comet Assay) Using Immortalized Non-Tumorigenic Human Epidermal HaCat Cells Olive tail moments and statistics experiments were performed using the HaCat cell line. Results showed reduced values of olive tail moments, similar to those values found for the cells that were not exposed to UVC radiation suggesting that under the assayed conditions the recombinant CPD-photolyase from *Hymenobacter* sp. UV11 reduced the JVC-DNA damage of HaCat cells almost completely.

These results wee supported by the statistic test (multiple comparison ANOVA assay), where 50 comets per treatment were counted in duplicate.

TABLE 2

| Test details | Mean 1 | Mean 2 | Mean Difference | Standard error for the difference | Significance | Summary |
|---|---|---|---|---|---|---|
| C+ vs. C− | 2.348 | 0.1655 | 2.182 | 0.03399 | Yes | **** |
| C+ vs. Photo_2 + BL | 2.348 | 0.26 | 2.088 | 0.03399 | Yes | **** |
| C+ vs. Photo_1.5 + BL | 2.348 | 0.2475 | 2.1 | 0.03399 | Yes | **** |

TABLE 2-continued

| Test details | Mean 1 | Mean 2 | Mean Difference | Standard error for the difference | Significance | Summary |
|---|---|---|---|---|---|---|
| C+ vs. Photo_1 + BL | 2.348 | 0.266 | 2.082 | 0.03399 | Yes | **** |
| C+ vs. Photo_1.5 Heat | 2.348 | 2.351 | −0.003 | 0.03399 | No | ns |
| C+ vs. Photo_1.5 | 2.348 | 2.137 | 0.151 | 0.03399 | Yes | * |
| C+ vs. Photo_1 | 2.348 | 2.251 | 0.097 | 0.03399 | No | ns |
| C− vs. Photo_2 + BL | 0.1655 | 0.26 | −0.0945 | 0.03399 | No | ns |
| C− vs. Photo_1.5 + BL | 0.1655 | 0.2475 | −0.082 | 0.03355 | No | ns |
| C− vs. Photo_1 + BL | 0.1655 | 0.266 | −0.1005 | 0.03399 | No | ns |
| C− vs. Photo_1.5 Heat | 0.1655 | 2.351 | −2.185 | 0.03399 | Yes | **** |
| C− vs. Photo_1.5 | 0.1655 | 2.197 | −2.031 | 0.03399 | Yes | **** |
| C− vs. Photo_1 | 0.1655 | 2.251 | −2.085 | 0.03399 | Yes | **** |
| Photo_2 + BL vs. Photo_1.5 + BL | 0.26 | 0.2475 | 0.0125 | 0.03399 | No | ns |
| Photo_2 + BL vs. Photo_1.5 + BL | 0.26 | 0.266 | −0.006 | 0.03399 | No | ns |
| Photo_2 + BL vs. Photo_1.5 Heat | 0.26 | 2.351 | −2.091 | 0.03399 | Yes | **** |
| Photo_2 + BL vs. Photo_1.5 | 0.26 | 2.197 | −1.937 | 0.03399 | Yes | **** |
| Photo_2 + BL vs. Photo_1 | 0.26 | 2.251 | −1.991 | 0.03399 | Yes | **** |
| Photo_1.5 + BL vs. Photo_1 + BL | 0.2475 | 0.266 | −0.0185 | 0.03399 | No | ns |
| Photo_1.5 + BL vs. Photo_1.5 Heat | 0.2475 | 2.351 | −2.103 | 0.03399 | Yes | **** |
| Photo_1.5 + BL vs. Photo_1.5 | 0.2475 | 2.197 | −1.949 | 0.03399 | Yes | **** |

Abbreviations are as follows: C1−, non-irradiated cells (non-damaged DNA); C2−, non-irradiated cells treated with endonuclease T4 V (basal DNA damage under normal conditions); C3−, UVC-irradiated cells (damaged DNA); C4−, non-irradiated cells treated with the recombinant photolyase (potential damage 5 produced by the recombinant photolyase); C+, UVC-irradiated cells treated with endonuclease T4 V (total damage of DNA); Photo_1, Photo_0.1 and Photo_0.02 are cells treated with 50 μl of 1, 0.1 and 0.02 mg/ml recombinant CPD photolyase.

Example 3—CPD-Repair Activity by Immunoassay

Immunochemical assay experiments, using monoclonal commercial antibodies that recognize CPDs (Table 3), also confirmed that the recombinant CPD-photolyase from *Hymenobacter* sp. UV11 was purified as an active DNA repairing enzyme. In these experiments, calf-thymus DNA that contains single stranded DNA, was used as substrate and the recombinant CPD-photolyase reduced the presence CPDs completely. In this assay, UVC-irradiated and non-photolyase treated DNA were used as reference or control experiments. We detected repair activity even by using 1 μg ml of the recombinant photolyase, which means that the purified enzyme was diluted 5000 fold for this experiment. When experiments were carried out in darkness or when the recombinant enzyme was denatured by heating, we did not detect repair activity. These results also show that the recombinant CPD-photolyase from *Hymenobacter* sp. UV11 has been purified as an active enzyme which requires light for its repair activity.

Results were supported by the statistic test One-way ANOVA ($p<0.05$).

TABLE 3

| Test details | Mean 1 | Mean 2 | Mean Difference | Standard error for the difference | Significance | Summary |
|---|---|---|---|---|---|---|
| C+ vs. C− | 2.348 | 0.1655 | 2.182 | 0.03399 | Yes | **** |
| C+ vs. Photo_2 + BL | 2.348 | 0.26 | 2.088 | 0.03399 | Yes | **** |
| C+ vs. Photo_1.5 + BL | 2.348 | 0.2475 | 2.1 | 0.03399 | Yes | **** |
| C+ vs. Photo_1 + BL | 2.348 | 0.266 | 2.082 | 0.03399 | Yes | **** |

TABLE 3-continued

| Test details | Mean 1 | Mean 2 | Mean Difference | Standard error for the difference | Significance | Summary |
|---|---|---|---|---|---|---|
| C+ vs. Photo_1.5 Heat | 2.348 | 2.351 | −0.003 | 0.03399 | No | ns |
| C+ vs. Photo_1.5 | 2.348 | 2.197 | 0.151 | 0.03399 | Yes | * |
| C+ vs. Photo_1 | 2.348 | 2.251 | 0.097 | 0.03399 | No | ns |
| C− vs. Photo_2 + BL | 0.1655 | 0.26 | −0.0945 | 0.03399 | No | ns |
| C− vs. Photo_1.5 + BL | 0.1655 | 0.2475 | −0.082 | 0.03399 | No | ns |
| C− vs. Photo_1 + BL | 0.1655 | 0.266 | −0.1005 | 0.03399 | No | ns |
| C− vs. Photo_1.5 Heat | 0.1655 | 2.351 | −2.185 | 0.03399 | Yes | **** |
| C− vs. Photo_1.5 | 0.1655 | 2.197 | −2.031 | 0.03399 | Yes | **** |
| C− vs. Photo_1 | 0.1655 | 2.251 | −2.085 | 0.03399 | Yes | **** |
| Photo_2 + BL vs. Photo_1.5 + BL | 0.26 | 0.2475 | 0.0125 | 0.03399 | No | ns |
| Photo_2 + BL vs. Photo_1.5 + BL | 0.26 | 0.266 | −0.006 | 0.03399 | No | ns |
| Photo_2 + BL vs. Photo_1.5 Heat | 0.26 | 2.351 | −2.091 | 0.03399 | Yes | **** |
| Photo_2 + BL vs. Photo_1.5 | 0.26 | 2.197 | −1.937 | 0.03399 | Yes | **** |
| Photo_2 + BL vs. Photo_1 | 0.26 | 2.251 | −1.991 | 0.03399 | Yes | **** |
| Photo_1.5 + BL vs. Photo_1 + BL | 0.2475 | 0.266 | −0.0185 | 0.03399 | No | ns |
| Photo_1.5 + BL vs. Photo 1.5 Heat | 0.2475 | 2.351 | −2.103 | 0.03399 | Yes | **** |
| Photo_1.5 + BL vs . Photo_1.5 | 0.2475 | 2.197 | −1.949 | 0.03399 | Yes | **** |
| Photo_1.5 + BL vs. Photo_1 | 0.2475 | 2.251 | −2.003 | 0.03399 | Yes | **** |
| Photo_1 + BL vs. Photo_1.5 Heat | 0.266 | 2.351 | −2.085 | 0.03399 | Yes | **** |
| Photo_1 + BL vs. Photo_1.5 | 0.266 | 2.197 | −1.931 | 0.03399 | Yes | **** |
| Photo_1 + BL vs. Photo_1 | 0.266 | 2.251 | −1.985 | 0.03399 | Yes | **** |
| Photo_1.5 Heat vs. Photo_1.5 | 2.351 | 2.197 | 0.154 | 0.03399 | Yes | * |
| Photo_1.5 Heat vs. Photo_1 | 2.351 | 2.251 | 0.1 | 0.03399 | No | ns |
| Photo_1.5 vs. Photo_1 | 2.197 | 2.251 | −0.054 | 0.03399 | No | ns |

Abbreviations are as follows: C−, non-irradiated calf thymus DNA (non-damaged DNA); C+, 10 Joules UVC-irradiated DNA (damaged DNA); Photo_1 + BL, Photo_1.5 + BL and Photo_2 + BL are UVC-irradiated DNA treated with 1, 1.5 and 2 µg/ml recombinant CPD-photolyase and blue light (BL); Photo_1.5 and Photo_1 are UVC-irradiated DNA treated with 1.5 and 1 µg/ml recombinant CPD-photolyase in darkness conditions, respectively; Photo_1.5 Heat is UVC-irradiated DNA treated with heat-inactivated recombinant CPD-photolyase (boiled for 10 min).

Example 4—Experiments Using the Recombinant 6,4-Bifunctional Photolyase as Repairing Enzyme Immunochemical assays, using monoclonal commercial antibodies that recognize 6,4-photoproducts (Table 4) and CPDs (Table 5), also confirmed that the recombinant 6,4-bifunctional photolyase from *Sphingomonas* sp. UV9 was purified as an active DNA repairing enzyme. In these experiments, we detected repair activity of both DNA lesions CPD and 6,4-photoproducts, even by using 1 µg ml$^{-1}$ of the recombinant 6,4-bifunctional photolyase.

These results Show that the recombinant 6,4-bifunctional photolyase from *Sphingomonas* sp. UV9 has been purified as an active enzyme and that this enzyme might repair both DNA lesions (CPD and 6,4-photoproducts).

6,4-Photoproduct-Repair Activity by Immunoassay

Experiments using the recombinant 6,4-bifunctional photolyase from *Sphingomonas* sp. UV9 as repairing enzyme. Immunodetection of 6,4-photoproducts. Results were supported by the statistic test One-way ANOVA ($p<0.05$).

TABLE 4

| Test details | Mean 1 | Mean 2 | Mean Difference | Standard error for the difference | Significance | Summary |
|---|---|---|---|---|---|---|
| C+ vs. C− | 2.348 | 0.1705 | 2.177 | 0.02328 | Yes | **** |
| C+ vs. 6.4 | 2.348 | 0.1925 | 2.155 | 0.02328 | Yes | **** |
| C− vs. 6.4 | 0.1705 | 0.1925 | −0.022 | 0.02328 | No | ns |

Abbreviations are as follows: C−, non-irradiated calf thymus DNA (non-damaged DNA); C+, 10 Joules UVC-irradiated DNA (damaged DNA); 6.4, DNA samples treated with the recombinant 6,4-bifunctional photolyase at a concentration of 2 mg/ml, as described above.

The CPD-Repair Activity by Immunoassay

Experiments using the recombinant 6,4-bi functional photolyase from *Sphingomonas* sp. UV9 as repairing enzyme. Immunodetection of CPD-photoproducts. Results were supported by the statistic test One-way ANOVA ($p<0.05$).

TABLE 5

| Test details | Mean 1 | Mean 2 | Mean Difference | Standard error for the difference | Significance | Summary |
|---|---|---|---|---|---|---|
| C+ vs. C− | 2.14 | 0.1655 | 1.974 | 0.1641 | Yes | *** |
| C+ vs. 6.4 | 2.14 | 0.4565 | 1.683 | 0.1641 | Yes | *** |
| C− vs. 6.4 | 0.1655 | 0.4565 | −0.291 | 0.1894 | No | ns |

Abbreviations are as follows: C−, non-irradiated calf thymus DNA (non-damaged DNA); C+, 10 Joules UVC-irradiated DNA (damaged DNA); 6.4, DNA samples treated with the recombinant 6,4-bifunctional photolyase at a concentration of 2 mg/ml, as described above.

Example 5—Method for the Qualitative Determination of CPD-Photolyase Activity With the aim of fully CPDs formation, the plasmid pUC13-2 was UVC-irradiated (1000 J m, 254 nm) using a Spectroline lamp (model ENF-260C/FE). The full radiation was evaluated by MseI digestion (1 µg of plasmid-DNA was digested with 1 Unit of the restriction enzyme for 1 h at 37° C., in a total reaction volume of 50 µl) and 1% agarose gel electrophoresis at room temperature, for 1 h at 60V, using TAE as running buffer (TAE, 40 mM Tris, 20 mM acetic acid, and 1 mM EDTA). DNA-restriction fragments were visualized by staining with ethidium bromide as follows: the gel was submerged in 0.5 µg/ml ethidium bromide for 30 min, washed with distilled water and visualized under UV light. DNA-damage was evidenced by the absence of the 780 kbp DNA fragment corresponding to the miniTn5 cassette. CPD-activity was evidenced by MseI digestion of UVC-irradiated pUC18-2 previously incubated with the CPD-photolyase at 1 µg/ml final concentration, at room temperature and blue light radiation, for 5 min for photoreduction and photorepair enzyme reactivation. The change in the electrophoretic profile of the MseI digested UVC-irradiated pUC18-2 plasmid as shown in FIG. 8 is evidence of CPDs reparation.

Example 6—Experiments Using the Recombinant 6,4-Photolyase as Repairing Enzyme Immunochemical assays, using monoclonal commercial antibodies that recognize 6,4-photoproducts (Table 6) confirmed that the recombinant 6,4-photolyase from *Sphingomonas* sp. UV9 was purified as an active DNA repairing enzyme. These results show that the recombinant 6,4-photolyase from *Sphingomonas* sp. UV9 has been purified as an active enzyme and that 6,4-photoproducts.

6,4-Photoproduct-Repair Activity by Immunoassay

Experiments using the recombinant 6,4-photolyase from *Sphingomonas* sp. UV9 as repairing enzyme. Immunodetection of 6,4-photoproducts. Results were supported by the statistic test One-way ANOVA ($p<0.05$).

TABLE 6

| Test details | Mean 1 | Mean 2 | Mean Difference | Standard error for the difference | Significance | Summary |
|---|---|---|---|---|---|---|
| C+ vs. C− | 0.4530 | 0.1434 | 0.3096 | 0.02192 | Yes | **** |
| C+ vs. 6.4 | 0.4530 | 0.1871 | 0.2659 | 0.02192 | Yes | **** |
| C− vs. 6.4 | 0.1871 | 0.1434 | 0.0437 | 0.02192 | Mo | ns |

Abbreviations are as follows: C−, non-irradiated calf thymus DNA (non-damaged DNA); C+, 10 Joules UVC-irradiated DNA (damaged DNA); 6.4, DNA samples treated with the recombinant 6,4-photolyase at a concentration of 2 mg/ml, as described above.

The invention claimed is:

1. A genetically modified microorganism comprising at least one gene encoding a photolyase selected from the group consisting of:
   an isolated nucleic acid molecule comprising the sequence of SEQ ID NO: 1;
   an isolated nucleic acid molecule containing the sequence of SEQ ID NO: 3;
   an isolated nucleic acid molecule containing the sequence of SEQ ID NO: 5.

2. The genetically modified microorganism of claim 1, wherein the genetically modified organism is a bacteria and the bacteria is *Escherichia coli*.

3. An isolated nucleic acid molecule comprising the sequence of SEQ ID NO: 1.

4. An isolated nucleic acid molecule comprising the sequence of SEQ ID NO: 3.

5. An isolated nucleic acid molecule comprising the sequence of SEQ ID NO: 5.

6. A recombinant photolyase comprising at least one gene encoding a photolyase that comprises the transformation of *Escherichia coli* with the host-vector comprising a DNA construct consisting of at least the sequence of an isolated nucleic acid molecule comprising the sequence of SEQ ID NO: 1, SEQ ID NO: 3 or SEQ ID NO: 5 operatively linked to a promoter and terminator sequences of the transcription, containing a histidine tag and Kanamycin resistance.

7. A pharmaceutical composition comprising the genetically modified microorganism from claim 1.

8. A cosmetic comprising the genetically modified microorganism from claim 1.

* * * * *